(12) United States Patent
Kessel et al.

(10) Patent No.: US 6,689,299 B2
(45) Date of Patent: Feb. 10, 2004

(54) PROCESS FOR PRODUCING SOLID CREATINE DOSAGE FORMS AND DOSAGE FORMS OBTAINABLE THEREBY

(75) Inventors: Knut Kessel, Mannheim (DE); Günter Scherr, Ludwigshafen (DE); Thomas Bogenstätter, Bad Dürkheim (DE); Gunther Berndl, Herxheim (DE); Jörg Breitenbach, Mannheim (DE)

(73) Assignee: BASF Aktiengesellschaft, Ludwigshaften (DE)

( * ) Notice: Subject to any disclaimer, the term of this patent is extended or adjusted under 35 U.S.C. 154(b) by 316 days.

(21) Appl. No.: 09/825,958

(22) Filed: Apr. 5, 2001

(65) Prior Publication Data

US 2001/0042936 A1 Nov. 22, 2001

(30) Foreign Application Priority Data

Apr. 6, 2000 (DE) .......................... 100 17 102

(51) Int. Cl.⁷ ................. B29C 43/08; A61K 31/195
(52) U.S. Cl. ............... 264/141; 264/210.2; 264/331.19; 424/439; 424/486; 514/565
(58) Field of Search ............... 264/141, 210.2, 264/280, 211, 204, 331.19; 424/439, 486; 514/565, 970

(56) References Cited

U.S. PATENT DOCUMENTS

| 4,801,460 A | 1/1989 | Goertz et al. ............... 424/465 |
| 4,880,585 A | 11/1989 | Klimesch et al. ............ 264/141 |
| 4,957,681 A | 9/1990 | Klimesch et al. ............ 264/211 |
| 5,073,379 A | 12/1991 | Klimesch et al. ............ 424/467 |
| 5,773,473 A * | 6/1998 | Green et al. ................. 514/565 |
| 6,172,114 B1 * | 1/2001 | McCabe ...................... 514/565 |
| 6,399,661 B1 * | 6/2002 | Golini ......................... 514/565 |
| 2002/0151593 A1 * | 10/2002 | Stitley, Jr. et al. | |

FOREIGN PATENT DOCUMENTS

| DE | 195 37 491 | 3/1997 |
| DE | 19537494 A1 * | 3/1997 |
| DE | 197 29 305 | 1/1999 |
| DE | 19729305 A1 * | 1/1999 |
| JP | 60 54 320 | 3/1985 |
| WO | WO 99/00122 | 1/1999 |

* cited by examiner

Primary Examiner—Mark Eashoo
(74) Attorney, Agent, or Firm—Keil & Weinkauf

(57) ABSTRACT

A process for producing solid creatine-containing dosage forms, wherein a) a mixture which comprises at least one thermoplastic, physiologically tolerated, water-soluble or water-swellable polymeric binder and creatine, and contains 1 to 20 mol of water per mol of creatine is prepared, b) the mixture is plasticated at or above the softening point of the polymeric binder, preferably with at least partial evaporation of the water, c) the plasticated mixture is shaped to dosage forms and cooled.

9 Claims, No Drawings

PROCESS FOR PRODUCING SOLID CREATINE DOSAGE FORMS AND DOSAGE FORMS OBTAINABLE THEREBY

A process for producing solid creatine dosage forms and dosage forms obtainable thereby.

The invention relates to a process for producing solid creatine-containing dosage forms and to the dosage forms obtainable thereby.

The amino acid derivative creatine occurs in nature in particular as creatine phosphate in vertebrate muscle. Creatine phosphate acts in this case as energy carrier in the cell for muscular contraction energy. Creatine is absorbed from the food or synthesized endogenously in the pancreas and liver. It can be isolated from natural sources or be synthesized by guanylation of sarcosine. Creatine is used as food supplement in the therapy of neuromuscular disorders (e.g. muscular dystrophy) and endocrinopathies associated with insufficient creatine storage and increased excretion in the urine. Besides the use in culture media and as flavor enhancer in spices, creatine is increasingly being employed as food supplement in sport to increase physical capacity and, in particular, in body building.

Creatine occurs in the form of a monohydrate which is stable under ambient conditions. The known pharmaceutical preparations of creatine always contain this monohydrate form. Thus, WO 99/00122 describes the production of creatine granules by mixing creatine monohydrate with an aqueous polyvinylpyrrolidone solution and other excipients. The moist granules are dried at 45° C. and compressed to tablets. The process has the disadvantage that several time-consuming and costly steps are necessary to obtain tablets. The resulting tablets contain 100 mg of creatine monohydrate in a tablet weighing 135 mg, equivalent to 5.0 mmol/g creatine tablet weight.

In addition, creatine dosage forms are commercially available in the form of two-piece gelatin capsules with a creatine monohydrate content of about 70%, equivalent to 4.7 mmol of creatine based on the weight of the capsule in g. The production and the filling of two-piece gelatin capsules are likewise time-consuming and costly.

The creatine content of these known dosage forms based on creatine monohydrate cannot be increased straightforwardly because the content of binder or the capsule shell as a proportion of the total weight cannot be reduced below a critical value without impairing the mechanical properties of the dosage form. Creatine monohydrate contains 12% by weight of water of crystallization. Since the water of crystallization has no physiological effect, it would be impossible to obtain solid dosage forms with a higher molar creatine content by use of a creatine hypohydrate or anhydrous creatine. However, these creatine forms are poorly defined and, moreover, hygroscopic. For this reason, they would lead to dosage forms which are unstable in the surrounding air.

A process which has been known for some time for producing solid pharmaceutical forms is the so-called melt calendering in which an active ingredient-containing, essentially solvent-free melt of a polymeric binder is extruded, and the extrudate is shaped to the desired drug form, for example in a calender with molding rolls, see EP-A-240 904, EP-A-240 906, EP-A-337 256 and EP-A-358 105. Polymers of N-vinylpyrrolidone or copolymers thereof, for example with vinyl acetate, in particular are employed as polymeric binder. The formation of the active ingredient-containing melt in this case is generally achieved at a temperature of about 150° C.

The use of melt calendering for producing solid creatine dosage forms has not been described to date. It is unavoidable in melt calendering that the active pharmaceutical ingredient is exposed to relatively high temperatures. Since creatine starts to undergo thermal decomposition, in particular to creatinine, at temperatures of about 80° C., it was not obvious to use melt calendering for producing creatine-containing dosage forms.

Surprisingly, it has been found that solid creatine dosage forms can be produced in a process which can be used economically on the industrial scale, comprises few process steps and makes it possible to produce stable creatine dosage forms with a high molar content of creatine.

The invention relates to a process for producing solid creatine-containing dosage forms, wherein
a) a mixture which comprises at least one thermoplastic, physiologically tolerated, water-soluble or water-swellable polymeric binder and creatine, and contains 1 to 20 mol of water per mol of creatine is prepared,
b) the mixture is plasticated at or above the softening point of the polymeric binder, preferably with at least partial evaporation of the water,
c) the plasticated mixture is shaped to dosage forms and cooled.

The invention additionally relates to the dosage forms obtainable by the process. It further relates to a creatine-containing solid dosage form comprising at least 3.3 mmol of creatine, based on the weight of the dosage form in g, in fine dispersion or molecular dispersion in a matrix composed of a thermoplastic, physiologically tolerated, water-soluble or water-swellable polymeric binder.

The term "solid dosage form" is intended to refer to a presentation which is suitable in particular for oral or rectal administration and has any desired forms such as, for example, tablets, coated tablets, pastilles, pellets, granules and the like.

The mixture prepared in step a) contains 1 to 20 mol, preferably 1 to 15 mol, in particular 3 to 10 mol, of water per mol of creatine. The water content is composed of the content bound to creatine as water of crystallization and the "free" water in the mixture. This water presumably on the one hand acts at elevated temperature as temporary plasticizer for the water-soluble or water-swellable polymeric binder, and on the other hand limits, through its enthalpy of vaporization, the thermal stress on the creatine.

The mixture can be prepared by starting from the dry, anhydrous components and mixing them with the required amount of water. However, it is more expedient to use creatine monohydrate, i.e. a creatine hydrate with 1 mol of water of crystallization per mol of creatine. Also suitable are creatine monohydrate forms which contain, beyond their content of water of crystallization, also unbound water which, for example, adheres as moisture to the surface of the crystallites or is trapped between the crystal system. Such forms are obtained when an aqueous suspension of creatine monohydrate, which is usually the initial result of chemical synthesis of creatine, is filtered or centrifuged. The filtration residue or centrifugation residue contains, for example, 5 to 50% by weight, usually 15 to 30% by weight, of adherent water which is not bound as water of crystallization. The use of the filtration residue or centrifugation residue with residual moisture has the additional advantage that drying to give creatine monohydrate is unnecessary.

Creatine is generally prepared industrially by guanylation of sarcosine, i.e. transfer of the guanyl radical (carbamimidoyl radical) to sarcosine or its salts. Suitable guanylating agents are O-alkylisourea salts, in particular O-methylisourea methyl sulfate (cf. JP 59000, DE 197 48 696 or DE-A 198 60 048.8) or cyanamide (cf. EP 0754 679).

The polymeric binder is usually employed in an essentially anhydrous form, i.e. preferably not as solution or dispersion. Many water-soluble or water-swellable polymeric binders absorb moisture on storage under ambient conditions. This results in an equilibrium moisture content of, for example, 1 to 5% by weight. These forms are regarded as "essentially anhydrous" for the present purposes.

In the process of the invention, creatine is embedded as a fine dispersion or molecular dispersion in a matrix of a water-soluble or water-swellable polymeric binder, preferably with formation of a solid solution. In this way there is stabilization of creatine hypohydrates (i.e. hydrates with less than 1 mol of water of crystallization per mol of creatine) or anhydrous creatine, so that dosage forms produced according to the invention are stable under ambient conditions even if they contain less than 1 mol of water per mol of creatine content.

Normally 15 to 70 g, preferably 40 to 70 g, of thermoplastic, physiologically tolerated, water-soluble or water-swellable polymeric binder are employed per mol of creatine. Preferably, the composition of the mixture is chosen so, and/or the amount of water evaporated in the plastication is such, that the plasticated mixture contains at least 3.3 mmol, preferably at least 4.2 mmol and, in particular, at least 5.1 mmol, e.g. 5.1 to 5.4 mmol, of creatine based on the weight of the plasticated mixture in g. The plasticated mixture preferably contains less than 1 mol of water per mol of creatine. The figures stated apply correspondingly to the resulting dosage forms.

Water-soluble or water-swellable polymeric binders contain units of hydrophilic monomers, where appropriate in conjunction with units of hydrophobic monomers. They can be assigned inter alia to the natural or modified polysaccharides; polyalkylene oxides which are solid at room temperature; homopolymers and copolymers of hydrophilic, ethylenically unsaturated monomers such as N-vinylamides, ethylenically unsaturated mono- and dicarboxylic acids, (meth)acrylamide, hydroxyalkyl (meth)acrylates and the like.

Examples of suitable binders are:

Polyvinylpyrrolidone (PVP), copolymers of N-vinylpyrrolidone (NVP) and vinyl esters, in particular vinyl acetate, copolymers of vinyl acetate and crotonic acid, partially hydrolyzed polyvinyl acetate, polyvinyl alcohol, poly(hydroxyalkyl acrylates), poly(hydroxyalkyl methacrylates), copolymers of methyl methacrylate and acrylic acid, polyacrylamides, polyethylene glycols, polyvinylformamide (where appropriate partially or completely hydrolyzed), cellulose esters, cellulose ethers, in particular methylcellulose and ethylcellulose, hydroxyalkylcelluloses, in particular hydroxypropylcellulose, hydroxyalkylalkylcelluloses, in particular hydroxypropylethylcellulose, cellulose phthalates, in particular cellulose acetate phthalate and hydroxypropylmethylcellulose phthalate, and mannans, in particular galactomannans. Of these, particular preference is given to polyvinylpyrrolidone, polyethylene glycol, copolymers of N-vinylpyrrolidone and vinyl esters, poly(hydroxyalkyl acrylates), poly(hydroxyalkyl methacrylates), alkylcelluloses and hydroxyalkylcelluloses, especially the polyvinylpyrrolidones and vinylpyrrolidone/vinyl acetate copolymers having the proprietary name Kollidon®.

Binders which are advantageously used as polymeric binders are those having a K value (according to Fikentscher, Cellulose-Chemie 13 (1932), p. 58–64, 71–74) in the range between 10 and 100, preferably between 15 and 80, in particular of about 30.

The most preferred polyvinylpyrrolidones have a K value in the range between 20 and 60.

Dosage forms of the invention preferably contain at least one of the polymeric binders described above. They may additionally contain other binders. The properties of the solid creatine-containing dosage forms of the invention can be varied through the nature of the binder chosen or the mixture of different binders. In particular, it is possible in this way to control the creatine release.

It should be possible to convert the polymeric binder into a plastic state in the complete mixture of all the components in the range from 50 to 150° C., preferably 60 to 130° C. The softening point is reduced if necessary by conventional pharmacologically acceptable plasticizing excipients. However, the mixture preferably contains no plasticizer. Examples of such plasticizers are:

long-chain alcohols, ethylene glycol, propylene glycol, glycerol, trimethylolpropane, triethylene glycol, butanediols, pentanols, such as pentaerythritol, hexanols, polyethylene glycols, polypropylene glycols, polyethylene/propylene glycols, silicones, aromatic carboxylic esters (e.g. dialkyl phthalates, trimellitic esters, benzoic esters, terephthalic esters) or aliphatic dicarboxylic esters (e.g. dialkyl adipates, sebacic esters, azelaic esters, citric and tartaric esters), fatty acid esters such as glycerol mono-, di- or triacetate or sodium diethyl sulfosuccinate, of which polyethylene glycols and polyethylene/propylene glycols are preferred.

The use of a plasticizer results in a decrease in the softening point of the polymeric binder. The formation of the plastic mixture and the shaping can thus take place at lower temperatures, thereby limiting the polymer molecular weight reduction and the thermal decomposition of the creatine. If plasticizers are used, they are employed in an amount of less than 30% by weight, usually 1 to 15% by weight, based on the polymer component.

In preferred embodiments, the dosage forms produced according to the invention comprise at least one sugar alcohol such as, for example, mannitol, sorbitol, xylitol and, in particular, isomalt. The sugar alcohol is preferably employed in an amount of from 10 to 60 g, in particular from 15 to 45 g, per mol of creatine. The inclusion of a sugar alcohol allows the melt viscosity of the plasticated mixture to be set in a defined manner in the stated temperature range. The sugar alcohol also acts as solubilizer and leads to faster creatine release.

Dosage forms obtained according to the invention may comprise pharmaceutically acceptable excipients. Such excipients may facilitate the production of the dosage form and/or modulate the properties thereof. Examples of conventional pharmaceutical excipients, whose total amount can be up to 100% by weight based on the polymeric binder are the abovementioned plasticizers;

extenders and bulking agents, such as silicates or diatomaceous earth, magnesium oxide, aluminum oxide, titanium oxide, methylcellulose, sodium carboxymethylcellulose, talc, sucrose, lactose, cereal or corn starch, potato flour, in particular in a concentration of from 0.02 to 50, preferably 0.20 to 20, % by weight, based on the total weight of the mixture;

lubricants, glidants and mold release agents such as magnesium, aluminum and calcium stearates, talc and silicones, and animal or vegetable fats, in particular in hydrogenated form and those which are solid at room temperature. These fats preferably have a melting point of 30° C. or above. Triglycerides of $C_{12}$, $C_{14}$, $C_{16}$ and $C_{18}$ fatty acids are preferred. Waxes, such as carnauba wax, can also be used. These fats and waxes may advantageously be admixed alone or together with mono- and/or diglycerides or phosphatides, in particular lecithin. The mono- and diglycerides are preferably derived from the abovementioned fatty acid types. The total amount of lubricants and mold release agents is preferably 0.1 to 10% by weight;

flow regulators, for example diatomaceous earths, in particular the silicone dioxides of high purity which have the proprietary name Aerosil®, in an amount of from 0.1 to 5% by weight based on the total weight of the mixture;

disintegrants, e.g. sodium starch glycolate;

dyes, such as azo dyes, organic or inorganic pigments or dyes of natural origin, preference being given to inorganic pigments in a concentration of from 0.001 to 10, preferably 0.5 to 3, % by weight, based on the total weight of the mixture;

stabilizers such as antioxidants, light stabilizers, hydroperoxide destroyers, radical scavengers, stabilizers against microbial attack;

it is also possible to add wetting agents, preservatives, adsorbents and mold release agents, and surfactants, preferably anionic and nonionic such as, for example, soaps and soap-like surfactants, alkyl sulfates and alkyl sulfonates, salts of bile acids, alkoxylated fatty alcohols, alkoxylated alkyl phenols, alkoxylated fatty acids and fatty acid glycerol esters, which may be alkoxylated, and solubilizers such as Cremophor (polyethoxylated castor oil), Gelucire, vitamin E TPGS and Tween (ethoxylated sorbitan fatty acid esters) (cf., for example, H. Sucker et al. Pharmazeutische Technologie, Thieme-Verlag, Stuttgart 1978).

The selection of suitable excipients is based on expert knowledge as described, for example, in Fiedler, H. B., Lexikon der Hilfsstoffe für Pharmazie, Kosmetik, und angrenzende Gebiete, 4th edition, Aulendorf: ECV-Editio-Cantor-Verlag (1996).

In the process of the invention for producing solid creatine-containing dosage forms, the components are usually first mixed together. The mixture is then preferably plasticated, i.e. converted to the plastic state, with at least partial evaporation of the water content. The sequence of the steps of mixing and plasticating is, however, not obligatory. The production and plastication of the mixture may also overlap to some extent or take place simultaneously in apparatuses suitable for this purpose.

The mixture is plasticated by heating, usually with additional input of mechanical energy, for example by kneading, mixing or homogenizing. The mixture is preferably plasticated at temperatures of from 50 to 150° C., particularly preferably from 60 to 130° C. The plastication takes place in an apparatus customary for this purpose. Extruders having, in a cylindrical housing, one or more rotatable axles equipped with kneading and/or conveying elements are particularly suitable. It is alternatively possible to employ heatable containers with agitator, for example kneaders. However, the plastic mixture is preferably formed by extrusion. The plastication process steps can be carried out in a known manner, for example as described in EP-A-0 240 904, EP-A-0 337 256, EP-A-0358 108, WO 97/15290 and WO 97/15291. The contents of these publications and, in particular, the statements contained therein about melt extrusion are incorporated herein by reference.

Extruders which can be employed in the process of the invention are single-screw machines, intermeshing screw machines or else multiscrew extruders, in particular twin-screw extruders, co-rotating or counter-rotating and, where appropriate, equipped with kneading disks. Since at least part of the water present in the mixture is evaporated during the extrusion, the extruders are generally equipped with an evaporation section. Particularly preferred extruders are those of the ZKS series from Werner und Pfleiderer.

The shaping to the dosage form before solidification can take place in a variety of ways, depending on the viscosity of the plastic mixture, for example by casting, injection molding, compression, nipping or calendering. This is done by conveying the plastic mixture described above to one or more shaping steps in the process of the invention. The conveying can take place by pressing, pumping, e.g. with gear pumps, or preferably with an extruder.

The first shaping step advantageously takes place when the extrudate emerges from the extruder through suitably shaped dies, draw plates or other orifices, e.g. through a breaker plate, a circular die or a slit die. This usually results in a continuous extrudate, preferably with a constant cross section, e.g. in the form of a ribbon or of a strand, preferably with a circular, oval, rounded or flat and broad cross section.

Suitable downstream shaping steps for extrudates are, for example, cold cut, i.e. the cutting or chopping of the extrudate after at least partial solidification, hot cut, i.e. the cutting or chopping of the extrudate while still in the plastic form, or pinching off the still plastic extrudate in a nip device. It is possible with hot or cold cut to obtain, for example, granules (hot or cold granulation) or pellets. Hot granulation usually leads to dosage forms (tablets or pellets) with a diameter of from 0.1 to 10 mm, while cold granulation normally leads to cylindrical products with a length to diameter ratio of from 1 to 10 and a diameter of from 0.5 to 10 mm.

It is possible in this way to produce monolayer but also, on use of coextrusion, open or closed multilayer drug forms, for example oblong tablets, coated tablets, pastilles and pellets.

The drug forms can be provided with a coating by conventional methods in a downstream process step. Suitable materials for film coatings are the polymers mentioned as polymeric binders, in particular polyacrylates, such as the Eudragit® types, cellulose esters such as the hydroxypropylcellulose phthalates, and cellulose ethers such as ethylcellulose, hydroxypropylmethylcellulose or hydroxypropylcellulose and gelatin. Further shaping steps may also follow, such as, for example, rounding off the pellets obtained by hot or cold cut using rounding-off devices as described in DE-A-196 29 753.

In a suitable embodiment, the plastic mixture is conveyed to a molding calender for the shaping. Suitable molding calenders normally have at least two molding rolls and/or belts, with at least one of the molding rolls and/or at least one of the belts having depressions to receive and shape the plastic mixture. It is preferred to use a molding calender with pairs of counter-rotating molding rolls, with at least one of the molding rolls having on its outer surface depressions for receiving and shaping the plasticated mixture. It is possible with the aid of these molding calenders to produce granules and tablets of any desired size and shape. Suitable molding calenders are disclosed, for example, in EP-A-0 240 904, EP-A-0 240 906 and WO 96/19962, and in EP-A-0 358 105, which are incorporated herein by reference.

The dosage forms of the invention are used, for example, as drugs for the therapy of diseases associated with deficient creatine storage or with increased creatine excretion. The creatine-containing dosage forms of the invention are additionally suitable as food supplements for enhancing performance in sport, especially in strength sport.

The following examples are intended to illustrate the present invention in detail but not restrict it.

The materials creatine monohydrate (BASF), isomalt F (Palatinit), Kollidon®K30 (polyvinylpyrrolidone or polyvidone or PVP; BASF), Explotab (sodium starch glycolate; Mendell, Patterson, N.Y.) used in the examples are commercial products.

EXAMPLE 1

500 mg oblong tablets containing 5.1 mmol of creatine per 1.0 g of tablet weight were produced as follows:

784 g of creatine monohydrate, 200 g of isomalt F and 100 g of Kollidon®K30 (polyvinylpyrrolidone) were homogeneously mixed for 1 minute and then extruded and calendered to 500 mg oblong tablets. The calendering of the extruded melt took place as described in EP-A 240 904.

The extrusion took place under the following conditions:

| Section 1 | 44° C. |
| Section 2 | 69° C. |
| Section 3 | 120° C. |
| Section 4 | 115° C. |
| Section 5 | 110° C. |
| Die | 114° C. |

The release of the active ingredient from the tablets was investigated by the paddle method (USA, pH change). It was 60% after 1 h, 80% after 2 h and 98% after 6 h.

EXAMPLE 2

784 g of creatine monohydrate, 200 g of isomalt F and 80 g of Kollidon®K30 (polyvinylpyrrolidone) and 20 g of Explotab were homogeneously mixed for 1 minute and then extruded and calendered to 500 mg oblong tablets.

The extrusion took place under the following conditions:

| Section 1 | 37° C. |
| Section 2 | 55° C. |
| Section 3 | 130° C. |
| Section 4 | 119° C. |
| Section 5 | 120° C. |
| Die | 115° C. |

The release of the active ingredient from the tablets was investigated via the paddle method (USA, pH change). It was 75% after 1 h, 90% after 2 h and 99% after 6 h.

In all the examples the by-products from rearrangement and decomposition reactions (e.g. creatine) were below the detection limit of 0.5% based on the creatine content.

We claim:

1. A process for producing solid creatine-containing dosage forms, wherein a) a mixture which comprises at least one thermoplastic, physiologically tolerated, water-soluble or water-swellable polymeric binder and creatine, and contains 1 to 20 mol of water per mol of creatine is prepared, b) the mixture is plasticated at or above the softening point of the polymeric binder, c) the plasticated mixture is shaped to dosage forms and cooled.

2. A process as claimed in claim 1, wherein the mixture is plasticated with at least partial evaporation of the water.

3. A process as claimed in claim 1, wherein the plasticated mixture comprises at least 3.3 mmol of creatine based on the mass of the plasticated mixture in g.

4. A process as claimed in claim 1, wherein the mixture is plasticated using an extruder.

5. A process as claimed in claim 1, wherein the plasticated mixture is shaped to dosage forms by means of a molding calender with pairs of counter-rotating molding rolls, at least one of which has on its outer surface depressions for receiving and shaping the plasticated mixture.

6. A process as claimed in claim 1, wherein the binder is selected from polyvinylpyrrolidone, polyethylene glycol, copolymers of N-vinylpyrrolidone and vinyl esters, poly(hydroxyalkyl acrylates), poly(hydroxyalkyl methacrylates), alkylcelluloses, hydroxyalkylcelluloses and mixtures thereof.

7. A process as claimed in claim 1, wherein the mixture comprises at least one sugar alcohol.

8. A creatine-containing solid dosage form obtainable by the process as claimed in claim 1.

9. A creatine-containing solid dosage form comprising at least 3.3 mmol of creatine, based on the weight of the dosage forming, in fine dispersion or molecular dispersion in a matrix composed of a thermoplastic, physiologically tolerated, water-soluble or water-swellable polymeric binder.

* * * * *